(12) United States Patent
Abrevaya et al.

(10) Patent No.: US 7,459,596 B1
(45) Date of Patent: Dec. 2, 2008

(54) NANOCRYSTALLINE SILICALITE FOR CATALYTIC NAPHTHA CRACKING

(75) Inventors: Hayim Abrevaya, Des Plaines, IL (US); Ben A. Wilson, Des Plaines, IL (US); Stephen T. Wilson, Des Plaines, IL (US); Suheil F. Abdo, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 463 days.

(21) Appl. No.: 11/189,311

(22) Filed: Jul. 26, 2005

(51) Int. Cl.
*C07C 4/02* (2006.01)
*C10G 11/00* (2006.01)
*C10G 11/02* (2006.01)

(52) U.S. Cl. ............... 585/653; 585/651; 585/652; 208/113; 208/114; 208/118; 208/120.01; 208/121; 208/122

(58) Field of Classification Search ......... 585/651–653; 208/113, 114, 118, 120.01, 121, 122
See application file for complete search history.

(56) References Cited

U.S. PATENT DOCUMENTS

| | | | |
|---|---|---|---|
| 5,026,935 A | 6/1991 | Leyshon et al. | 585/315 |
| 5,026,936 A | 6/1991 | Leyshon et al. | 585/315 |
| 5,043,522 A | 8/1991 | Leyshon et al. | 585/651 |
| 6,118,035 A * | 9/2000 | Fung et al. | 585/653 |
| 6,183,699 B1 | 2/2001 | Lomas | 422/145 |
| 6,867,341 B1 * | 3/2005 | Abrevaya et al. | 585/650 |
| 7,314,964 B2 * | 1/2008 | Abrevaya et al. | 585/651 |

FOREIGN PATENT DOCUMENTS

| | | |
|---|---|---|
| EP | 109059 B1 | 11/1983 |
| EP | 109060 B1 | 11/1983 |

* cited by examiner

*Primary Examiner*—Glenn Caldarola
*Assistant Examiner*—In Suk Bullock
(74) *Attorney, Agent, or Firm*—Arthur E Gooding

(57) ABSTRACT

A method is provided for converting a hydrocarbon feedstock in the naphtha boiling range to light olefins. The method includes contacting the hydrocarbon feedstock with a zeolitic material having a crystal size from 50 to 300 nanometers, having a silica to alumina ratio greater than 200 and where the zeolitic material has a silicalite structure.

20 Claims, 1 Drawing Sheet

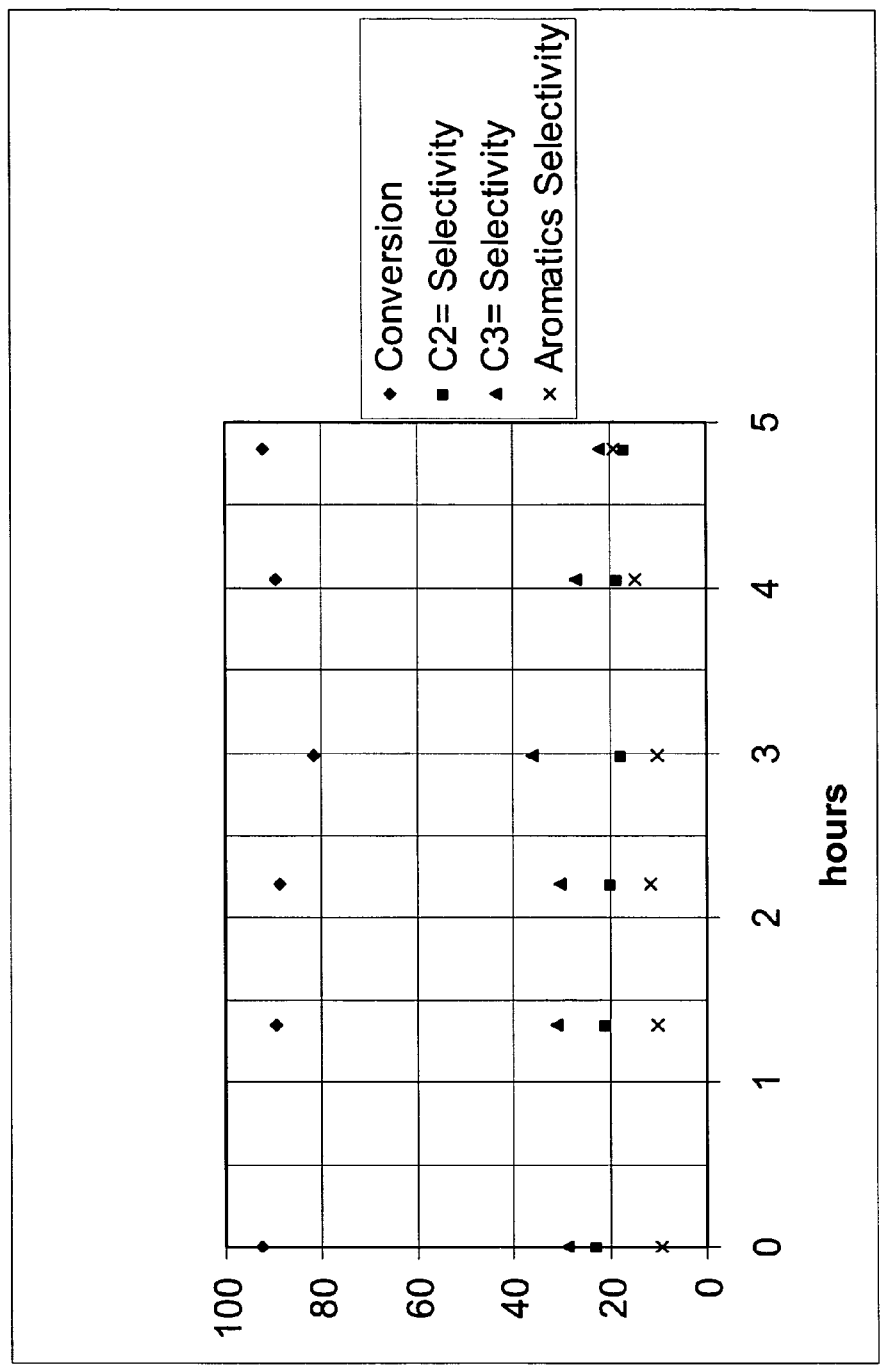

US 7,459,596 B1

NANOCRYSTALLINE SILICALITE FOR CATALYTIC NAPHTHA CRACKING

FIELD OF THE INVENTION

The present invention relates to a process for the production of light olefins from a naphtha feed stream. This invention also relates to an improved zeolite used in the process for producing light olefins.

BACKGROUND OF THE INVENTION

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces most of the ethylene and some propylene. One of the disadvantages of steam cracking is the low ratio of propylene to ethylene. Hydrocarbons used as feedstock for light olefin production include natural gas, petroleum liquids, and carbonaceous materials including coal, recycled plastics or any organic material.

An ethylene plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical ethylene separation section of an ethylene plant containing both cryogenic and conventional fractionation steps to recover an ethylene product with a purity exceeding 99.5% ethylene is described in an article by V. Kaiser and M. Picciotti, entitled, "Better Ethylene Separation Unit." The article appeared in HYDROCARBON PROCESSING MAGAZINE, November 1988, pages 57-61 and is hereby incorporated by reference.

Methods are known for increasing the conversion of portions of the products of the ethylene production from a zeolitic cracking process to produce more propylene by a disproportionation or metathesis of olefins. Such processes are disclosed in U.S. Pat. No. 5,026,935 and U.S. Pat. No. 5,026,936 wherein a metathesis reaction step is employed in combination with a catalytic cracking step to produce more propylene by the metathesis of $C_2$ and $C_4$ olefins obtained from cracking. The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 100 wt-% paraffins having 4 or more carbon atoms per molecule and 0 to 60 wt-% olefins having 4 more carbon atoms per molecule. In U.S. Pat. No. 5,043,522, it is disclosed that the preferred catalyst for such a zeolitic cracking process is an acid zeolite, examples includes several of the ZSM-type zeolites or the borosilicates. Of the ZSM-type zeolites, ZSM-5 was preferred. It was disclosed that other zeolites containing materials which could be used in the cracking process to produce ethylene and propylene included zeolite A, zeolite X, zeolite Y, zeolite ZK-5, zeolite ZK-4, synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred alkali exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina atomic ratio less than or equal to 300 at a temperature from 400 to 600° C. The ZSM-5 or ZSM-11 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having 4 carbon atoms are oligomerized to facilitate the removal of paraffins such as butane and particularly isobutane which are difficult to separate from $C_4$ olefins by conventional fractionation. In a related European Patent No. 109,060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500 to 600° C. and at a space velocity of from 5 to 200 kg/hr of butenes per kg of pure zeolitic compound. The European Patent No. 109,060B1 discloses the use of silicalite-1 in an ion-exchanged, impregnated, or co-precipitated form with a modifying element selected from the group consisting of chromium, magnesium, calcium, strontium and barium.

Generally, the heavier olefins having six or more carbon atoms per molecule which are produced in commercial ethylene plants are useful for the production of aromatic hydrocarbons. Portions of the olefin product include olefins with four carbon atoms per molecule. This portion includes both mono-olefins and di-olefins and some paraffins, including butane and iso-butane. Because the portion with four carbon atoms per molecule is generally less valuable and requires significant processing to separate di-olefins from the mono-olefins, processes are sought to improve the utilization of this portion of the ethylene plant product and enhancing the overall yield of ethylene and propylene.

It is difficult in naphtha cracking to obtain high selectivity to ethylene and propylene, while maintaining high conversion. Improvements in catalysts and processes that accomplish this are therefore desirable.

SUMMARY OF THE INVENTION

The present invention is a process for catalytic cracking of naphtha to light olefins. The process comprises contacting that fresh naphtha stream with a catalyst under reaction conditions. The catalyst comprises a molecular sieve with intersecting 10 member-rings channels, having a high silica to alumina ratio and a small crystal size. The silica to alumina ratio is greater than 200 and the average crystal size is from 30 nanometers to 300 nanometers. The present invention produces a higher conversion and selectivity for ethylene and propylene over prior catalysts, while having the additional benefit of low methane production and low coking during the cracking process.

In one embodiment, the process comprises contacting a recycle stream, in addition to the fresh naphtha, with the catalyst under reaction conditions. The recycle stream is between 5% and 70% by volume of the fresh naphtha stream.

Additional objects, embodiments and details of this invention can be obtained from the following drawing and detailed description of the invention.

BRIEF DESCRIPTION OF THE DRAWING

The FIGURE shows the stability of nano-silicalite.

DETAILED DESCRIPTION OF THE INVENTION

The demand for light olefins is increasing. Because of that demand, new processes and catalysts for improving the production of light olefins is important. Increasing the yield by even a small percentage can have a significant economic effect. The present invention provides for a process that generates an increase in light olefin, especially ethylene and propylene, yields from naphtha feedstocks. The process includes contacting a naphtha feedstock with a catalyst at reaction conditions, to crack larger paraffinic, naphthenic and larger olefinic molecules to smaller olefinic molecules while limiting the amount of aromatics formed. Optionally, the process includes feeding a recycle stream with the fresh naphtha feed stream for contact with the catalyst at reaction conditions. When a recycle stream is included with the fresh naphtha, it is preferred that the recycle stream is between 5% and 70% by volume of the naphtha.

The catalyst for use in this invention is a molecular sieve having a crystal structure with intersecting 10 membered-ring pore channels, and with an average crystal size from about 30 nanometers to about 300 nanometers, and the crystal has a silica to alumina ratio ($SiO_2:Al_2O_3$) greater than about 200. The crystalline structure of the molecular sieve can be an MFI, an MEL, an NES, an SFG, an MWW, or an ITH structure. A preferred molecular sieve is silicalite (MFI). Catalysts with NES structure include NU-87 and SSZ-37, catalysts with SFG structure includes SSZ-58, catalysts with MWW structure include MCM-22 and UZM-8, and catalysts with ITH structure include ITQ-13.

The crystals preferably have a size from about 50 nanometers to about 100 nanometers, with high silica to alumina ratios. Preferred silica to alumina ratios are greater than 300, with a more preferred ratio greater than 400, and a most preferred ratio greater than 1000. The catalyst crystals of the present invention can have the external surface acid site neutralized, thereby limiting the amount of activity on the external surface of the catalyst.

The naphtha components contact and react with the acid sites of the catalyst. The structure, size and acid site distribution contribute to the types of reactions the naphtha components undergo. The preferred reactions are the production of light olefins from the naphtha, and in particular, the preferred components of ethylene and propylene. The cracking of naphtha is a complex set of reactions that generate lighter hydrocarbon molecules. Improvements in the catalyst enable more control over the selection of products and a reduction in undesirable products or effects from the reactions. Undesirable products include methane and coke. Methane is a low value product and coke reduces the effectiveness of the catalyst while having no value as a product on the catalyst. Low coking enables longer use of the catalyst before regeneration and provides for lower cost operation. The present invention provides a catalyst with substantially reduced coking during the cracking process, and a reduction in methane production.

It is preferred to have good contact between the naphtha and catalyst, but not to have extended contact time between ethylene and propylene with the active sites in the catalyst. This can be achieved through limiting the size of the catalyst crystals, and by controlling the pore sizes and acid site distribution on the catalyst.

The invention comprises contacting a naphtha feedstream, in gaseous form, with a catalyst as described above. For example, the contacting of the naphtha with the catalyst can be carried out in a fluidized catalytic cracking (FCC)-type reactor. The process then entails feeding the hot catalyst and the vaporized, preheated naphtha into a reactor vessel, where the catalyst mixes with the gas and is entrained with the gas, and produces a gas-catalyst mixture that reacts under operating conditions to produce a product gas and a used catalyst. The choice of reactor can be any fluidized-type of reactor for intimately mixing the naphtha feedstream with the catalyst. Reactors of this type are well known to those skilled in the art. A fluidized reactor usable in this invention is described in U.S. Pat. No. 6,183,699, which is incorporated by reference in its entirety. The product gas and used catalyst exit the reactor where the catalyst and gas are separated. The separation process of gas and catalyst is well known to those skilled in the art. Following the separation of ethylene, propylene and aromatics, the unconverted naphtha, plus ethane, propane, butane and butanes can be recycled back to the reactor to make more ethylene and propylene.

Alternate feedstocks for cracking to light olefins include gas oil, vacuum gas oil, and Fischer-Tropsch wax. Preferably, the feedstock has been processed to remove aromatics. Optionally, the present invention can be incorporated into a system that includes product stream separation and recycle of uncracked components from the product streams.

The reaction process operating conditions include temperatures between about 550° C. to about 700° C. A preferred temperature for operating the process is to be in the range from about 600° C. to about 675° C. with a more preferred operating temperature of about 650° C. to about 670° C. The reaction process operation conditions further include hydrocarbon partial pressures between about 100 kPa (15 psia) to about 690 kPa (100 psia). Lower range can be as low as 17 kPa (2.5 psia).

The catalyst and vaporized feedstock are fed into the reactor vessel having a mass ratio of catalyst to hydrocarbons of at least 15, and preferably a mass ratio of at least 25. To obtain the proper flow conditions additional gas can be added to the reactor. The additional gases are a diluent and can be any non-oxidative gas that facilitates obtaining the proper flow conditions. The diluent gases include, but are not limited to nitrogen, argon, carbon dioxide, steam, methane and mixtures of non-oxidative gases. The diluent gases can be added to the vaporized naphtha feedstream on a volumetric basis from zero up to about five times the naphtha feedstream molar flow rate. Adding a diluent, such as steam or an inert gas, lowers the partial pressure, while maintaining the operating temperature and pressure of the system.

The process can also be carried out as a batch process, with the contact time varying from about 0.1 seconds to about 5 hours and preferably from about 0.1 seconds to about 0.1 hour. The longer contact times are used at lower temperatures while shorter times are used at higher temperatures, assuming all other process variables are equal.

Further, the process can also be carried out in a continuous mode in a fixed bed reactor or in a fixed fluidized-bed reactor. When the process is carried out in a fixed bed-type reactor, the weight hourly space velocity (WHSV) based on the total feed, including any diluents, can vary from about 2 $hr^{-1}$ to about 200 $hr^{-1}$ and preferably from about 10 $hr^{-1}$ to about 100 $hr^{-1}$. As is understood in the art, the weight hourly space velocity is the weight flow of the feed divided by the catalyst weight.

The catalysts of the present invention can be formed by hydrothermal crystallization of the nano-silicalite, followed by NH$_4$-exchange and calcinations steps to remove Na+ and structure directing agent. The product was characterized by XRD at each step of the preparation. The final product was characterized further by elemental analysis using ICP, N$_2$ sorption, and transmission electron microscopy (TEM) to check the crystal size and distribution.

The typical preparation of nano-silicalite is as follows. A first solution is made comprising 2.16 grams of aluminum tri-sec-butoxide and 451.1 grams of tetraethylorthosilicate by mixing in a beaker for 10 minutes with a mechanical mixer at room temperature. A second solution is made comprising 0.68 grams of NaOH pellets and 215.8 grams of 40% tetrapropylammonium hydroxide in 680.3 grams of deionized water. The first solution was placed in a bottle, and the second solution was added with stirring creating a mixed solution. The bottle was closed and the mixed solution was mixed further using a magnetic stir bar at room temperature for 24 hours, resulting in a clear solution. The clear solution was sealed in TEFLON™ bottles and heated statically in a 100° C. oven for 72 hours to crystallize. The product solid was recovered and washed by centrifuge and air dried. The XRD verified a pure MFI framework type. For testing purposes the crystals were subject to a 1-stage ammonium nitrate exchange at 80° C. for 16 hours, followed by a 2-stage ammonium nitrate exchange at 75° C. for 24 hours, and then calcined in dry air at 500° C. for 2 hours. The final product had a Si/Al$_2$ ratio of 567, an N$_2$ micropore volume of 0.153 cc/g, and a crystal size of about 50-100 nm.

EXAMPLE 1

Nano-silicalite was used in catalytic naphtha cracking tests against a coventional silicalite catalyst with a high silica/alumina ratio, and a ZSM-5 with a relatively low silica/alumina ratio. The conventional silicalite catalyst had crystals 10 to 20 times the characteristic size of those in the nano-silicalite. The conditions of the experiments were: reactor inlet temperatures of about 650° C., and inlet total pressure of about 120 kPa (3 psig). The ratio of catalyst to naphtha feedstream based on mass was about 40 in a fixed bed reactor. The injection time for the feed over the catalyst was 48 seconds. This experiment simulated an FCC-type operation where the molar ratio of diluent nitrogen to naphtha feedstream was 2.6.

TABLE 1

Catalysts

| Zeolite | % zeolite in catalyst | Si/Al$_2$ ratio | morphology of crystals | micropore volume, cc/g (zeolite only) |
|---|---|---|---|---|
| Nano-Silicalite | 100 | 567 | 50-100 nm | 0.153 |
| Silicalite | 100 | 348 | 1-2 micron cubes and cylinders | 0.173 |
| ZSM-5 | 80 | 38 | 1-2 micron cubes and cylinders | 0.167 |

The results from pulse micro-reactor tests of naphtha cracking yielded good results for the nano-silicalite catalyst. Under all conditions tested, nano-silicalite's activity and/or selectivity were better than conventional silicalite for which the crystal size was larger and ZSM-5 catalyst for which the crystal size was larger and the silica/alumina ratio was lower. The results of the tests, as shown in Table 2, showed higher conversion, higher average selectivities of ethylene and propylene, higher ratios of propylene to ethylene, and lower methane yields for nano-silicalite. In addition, in the experiments for this series, the nano-silicalite exhibited substantially zero coking during the cracking process. Without being bound by any theory, it is believed that the smaller size of crystals in combination with high Si/Al$_2$ ratio yields the unexpected improvement due to lower residence time of primary products in the pores of the catalyst in contact with the acid sites.

TABLE 2

Average selectivities from experiments

| Catalyst | Nano-silicalite | Silicalite | ZSM-5 |
|---|---|---|---|
| conversion, % | 94.0 | 89.1 | 94.1 |
| selectivities, % | | | |
| Methane | 6.0 | 7.2 | 16.6 |
| Ethylene | 29.3 | 29.9 | 13.7 |
| Ethane | 6.4 | 7.1 | 11.0 |
| Propylene | 24.4 | 22.3 | 4.1 |
| Propane | 5.3 | 5.3 | 0.8 |
| butanes + butenes | 6.7 | 5.2 | <0.1 |
| Aromatics | 20.8 | 21.3 | 49.0 |
| carbon monoxide | 0.1 | 0.2 | 0.3 |
| Hydrogen | 1.0 | 0.9 | 2.4 |
| Coke | 0 | 0.6 | 2.5 |
| Sum | 100 | 100 | 100.4 |
| ethylene + propylene | 53.7 | 52.2 | 17.8 |

EXAMPLE 2

FCC-type catalytic naphtha cracking tests were run with naphtha injected using nano-silicalite. The reactor system had catalyst introduced at 650° C. and at 168 kPa (10 psig) total pressure. The naphtha was reacted for 3 seconds with no diluent gas, followed by an injection of a purge gas, N$_2$, to remove the products from the reaction zone. The product was collected in a heated glass syringe and then injected into the on-line GCs for analysis. A series of experiments involved studying the effect of the silica to alumina ratio on per pass conversion and selectivity.

TABLE 3

Performance vs. silica/alumina ratio

| Si/Al$_2$ ratio | 634 | 819 | 1130 | 1430 |
|---|---|---|---|---|
| conversion, % | 91.4 | 90.3 | 85.7 | 87.5 |
| selectivities, % | | | | |
| Methane | 3.8 | 3.5 | 3.2 | 3.3 |
| Ethane | 6.0 | 5.6 | 5.3 | 5.5 |
| Ethylene | 23.7 | 23.5 | 21.1 | 23.0 |
| Propane | 7.5 | 8.1 | 6.3 | 6.6 |
| Propylene | 31.0 | 32.1 | 36.7 | 35.5 |
| total C4s | 12.9 | 13.8 | 15.6 | 14.6 |
| C10+ | 2.5 | 2.8 | 4.6 | 3.8 |
| Aromatics | 11.6 | 9.8 | 6.6 | 7.0 |
| Hydrogen | 0.8 | 0.8 | 0.6 | 0.7 |
| Coke | 0.2 | 0 | 0 | 0 |
| Sum | 100 | 100 | 100 | 100 |
| ethylene + propylene | 54.7 | 55.6 | 57.8 | 58.5 |
| propylene:ethylene | 1.31 | 1.37 | 1.73 | 1.54 |

Table 3 shows the favorable effect of increasing silica to alumina ratio for catalytic naphtha cracking when the silicalite catalyst crystals are kept in the nanometer size range. While there was a slight decrease in the conversion per pass, there was an increase in the selectivity for ethylene and propylene and an increase in the ratio of propylene to ethylene.

The improved selectivity leads to an increase in the projected overall yield following recycle of unconverted naphtha and other less reactive streams, i.e. propane, butane and butenes. The higher the silica to alumina ratios for nano-silicalite, the more improved is the catalyst over the catalysts currently used for the catalytic cracking of naphtha.

EXAMPLE 3

Nano-silicalite was tested for an FCC-type catalytic naphtha cracking processes, and was compared with conventional steam cracking. The steam cracking performance was simulated using Pycos. The catalytic naphtha cracking reaction conditions were a pressure about 168 kPa (10 psig), a temperature for the nano-silicalite experiments of about 650° C. at inlet, and with no diluent gas used in these experiments. The injection time for the feed was 3 seconds, and the catalyst to naphtha feed ratio was 40. The steam cracking was simulated at a temperature of 835° C. with a steam to naphtha ratio, by weight, of 0.4.

TABLE 4

Comparison with steam cracking

| Catalyst | Steam Cracking | Nano-silicalite ($Si/Al_2 = 634$) |
|---|---|---|
| Conversion, % | 91.3 | 91.4 |
| Selectivities, % | | |
| Methane | 17.2 | 3.8 |
| C2, C3 acetylenes | 1.5 | Not detected |
| Ethylene | 33.7 | 23.7 |
| Ethane | 4.1 | 6.0 |
| Propylene | 18.5 | 31.0 |
| Propane | 0.4 | 7.5 |
| Butadienes | 5.7 | Not detected |
| Butylenes | 5.2 | 11.0 |
| Butanes | 0 | 1.9 |
| Aromatics | 8.5 | 11.6 |
| Coke | Low | 0.2 |
| Carbon oxides | Low | 0 |
| Hydrogen | 1.1 | 0.8 |
| C10+ | 4.1 | 2.5 |
| Total | 100 | 100 |
| Ethylene + propylene | 52.2 | 54.7 |
| Propylene:ethylene | 0.55 | 1.31 |

The nano-silicalite gave improved selectivity of ethylene plus propylene over the steam cracking, but more importantly there was a significant decrease in methane production and selectivities to highly unsaturated olefins, accompanied by a significant increase in the propylene to ethylene ratios. This occurred with the added benefit of operating at lower temperatures, which could provide for lower utility costs in operation of naphtha cracking units.

EXAMPLE 4

Stability of a catalyst is important for its usefulness and the economics of using the catalyst. A continuous operation was performed and the results for nano-silicalite indicate that conversion and selectivity remained consistently high for many hours of operation, as shown in the FIGURE. The results from injections at roughly hourly intervals over a 5 hour period products show substantially the same conversions and selectivities for a nano-silicalite having a $Si/Al_2$ of 1100. The process was carried out with a steam:hydrocarbon weight ratio of 0.6, at a temperature of 650° C., and a pressure of 35 psia. The nano-silicalite was found to be very stable for the conditions under which continuous operation was carried out.

EXAMPLE 5

The nano-silicalite was also tested for regenerability. At the $Si/Al_2$ ratio of 630, the catalyst was used in the test as new, fresh catalyst, and then regenerated to remove carbon build-up on the catalyst. The tests were performed in an FCC-type system, and in a continuous type operation. The following table 5 shows the conversion percentage for fresh catalyst, and for regenerated catalyst, and the selectivity of ethylene plus propylene for the catalyst when fresh and regenerated. As can be seen, the catalyst is regenerable to comparable levels for conversion and selectivity as with fresh catalyst.

TABLE 5

Regenerability

| | Fresh, conversion % | Fresh, selectivity % | Carbon burned, conversion % | Carbon burned, selectivity % |
|---|---|---|---|---|
| Silicalite, $Si/Al_2 = 630$ FCC-type Performance | 93 | 54 | 92 | 55 |
| Silicalite, $Si/Al_2 = 630$ Peak Performance in continuous mode | 91 | 47 | 88 | 52 |

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for selective catalytic cracking of naphtha to light olefins comprising contacting a naphtha feedstock stream with a catalyst at reaction conditions to produce ethylene and propylene, the catalyst comprising a molecular sieve having intersecting 10 membered-ring channels with an average crystal size from about 30 nanometers to about 300 nanometers, and having a silica to alumina ratio greater than about 200.

2. The process of claim 1 wherein the light olefins comprise ethylene and propylene.

3. The process of claim 1 wherein the crystal size is from about 50 nanometers to about 100 nanometers.

4. The process of claim 1 wherein the molecular sieve has a silica to alumina ratio greater than about 300.

5. The process of claim 4 wherein the molecular sieve has a silica to alumina ratio greater than about 400.

6. The process of claim 5 wherein the molecular sieve has a silica to alumina ratio greater than about 1000.

7. The process of claim 1 wherein the reaction conditions include temperatures in the range from about 550° C. to about 700° C.

8. The process of claim 7 wherein the reaction conditions include partial pressures of the hydrocarbons in the range from about 17 kPa (2.5 psia) to about 690 kPa (100 psia).

9. The process of claim 1 wherein the external surface of the catalyst has neutralized acid sites.

10. The process of claim 1 further comprising contacting a recycle stream with the catalyst at reaction conditions between 5 vol. % and 70 vol. % of the naphtha feedstream.

11. The process of claim 1 wherein the catalyst and feedstock are fed into a reaction conduit to produce a mixture of solid catalyst particles and gaseous fluids.

12. The process of claim 11 wherein the reaction conditions include a catalyst to naphtha feedstock stream ratio of at least 15.

13. The process of claim 11 wherein the reaction conditions include a catalyst to naphtha feedstock stream ratio of at least 30.

14. The process of claim 1 further comprising adding a steam diluent, wherein the steam diluent is fed in a volume ratio to the naphtha feedstock in the range from greater than 0 to about 5.

15. The process of claim 1 further comprising adding a non-oxidative diluent gas, wherein the diluent gas is fed in a volume ratio to the naphtha feedstock stream in the range from greater than 0 to about 5.

16. The process of claim 15 wherein the non-oxidative diluent gas is selected from the group consisting of nitrogen, argon, carbon dioxide, steam, and mixtures thereof.

17. The process of claim 1 wherein the molecular sieve has either an MFI structure, an MEL structure, an NES structure, an SFG structure, an MWW structure, or an ITH structure.

18. The process of claim 17 wherein the molecular sieve is silicalite.

19. The process of claim 1 wherein the catalyst is disposed in a fixed bed reactor, fixed fluidized-bed reactor or circulating fluidized-bed reactor.

20. The process of claim 19 wherein the reaction conditions include weight hourly space velocities from about $2\,\mathrm{hr}^{-1}$ to about $200\,\mathrm{hr}^{-1}$.

* * * * *